(12) United States Patent
Doleschal et al.

(10) Patent No.: US 7,810,186 B2
(45) Date of Patent: Oct. 12, 2010

(54) DEVICE AND METHOD FOR MOTORIZED SUPPORT OF A PATIENT POSITIONING FACILITY

(75) Inventors: Stefan Doleschal, Grafenwöhr (DE); Tobias Hoth, Pegnitz (DE)

(73) Assignee: Siemens Aktiengesellschaft, Munich (DE)

( * ) Notice: Subject to any disclaimer, the term of this patent is extended or adjusted under 35 U.S.C. 154(b) by 153 days.

(21) Appl. No.: 11/663,694

(22) PCT Filed: Sep. 20, 2005

(86) PCT No.: PCT/EP2005/054711

§ 371 (c)(1),
(2), (4) Date: Mar. 22, 2007

(87) PCT Pub. No.: WO2006/034979

PCT Pub. Date: Apr. 6, 2006

(65) Prior Publication Data

US 2008/0098526 A1    May 1, 2008

(30) Foreign Application Priority Data

Sep. 30, 2004   (DE) .................... 10 2004 047 615

(51) Int. Cl.
*A47B 13/00*  (2006.01)
(52) U.S. Cl. .......................................... 5/601; 378/205
(58) Field of Classification Search .................. 5/601, 5/943, 600, 616; 378/209, 208, 205; 180/19.1, 180/19.3
See application file for complete search history.

(56) References Cited

U.S. PATENT DOCUMENTS

| 5,210,893 | A | * | 5/1993 | Uosaki et al. ................... 5/601 |
| 5,751,788 | A | * | 5/1998 | Khutoryansky et al. ..... 378/197 |
| 5,878,112 | A | * | 3/1999 | Koertge ....................... 378/209 |
| 6,045,262 | A | * | 4/2000 | Igeta et al. ................... 378/209 |
| 6,499,159 | B1 |   | 12/2002 | Schmitt et al. |
| 6,668,403 | B2 | * | 12/2003 | Seufert .......................... 5/601 |

FOREIGN PATENT DOCUMENTS

| DE | 199 29 654 C1 | 5/2001 |
| EP | 0 712 606 A1 | 5/1996 |

\* cited by examiner

*Primary Examiner*—Robert G Santos
*Assistant Examiner*—Nicholas Polito
(74) *Attorney, Agent, or Firm*—Brinks, Hofer, Gilson & Lione

(57) ABSTRACT

A device and method for motorized support of patient positioning are provided. The position of a patient bed and the setting of an electric motor drive are recorded which may differ due to elasticity and/or flexibility of the bed drive. A control signal for the electric motor drive is generated depending on the position of the patient bed and the setting of the electric motor drive. The drive can thus be activated for servo-support in case the patient bed is manually displaced, whereby the control signal is generated depending on a change in position of the patient bed, which does not correspond to a simultaneous change in the setting of the electric motor drive.

21 Claims, 2 Drawing Sheets

DEVICE AND METHOD FOR MOTORIZED SUPPORT OF A PATIENT POSITIONING FACILITY

The present patent document is a §371 continuation of PCT Application Serial Number PCT/EP2005/054711, filed Sep. 20, 2005, designating the United States, which is hereby incorporated by reference. This patent document also claims the benefit of DE 10 2004 047 615.2, filed Sep. 30, 2004.

BACKGROUND

The present embodiments relate to a device for motorized support of a patient positioning facility.

Patient positioning facilities are used in conjunction with medical diagnosis or therapy devices, for example, computer tomography devices, magnetic resonance devices, x-ray devices, x-ray therapy devices or ultrasound devices. Patient positioning facilities are used to position a patient or other object in the effective range of the medical device. The effective range of imaging diagnostic devices is the scanning range. To generate a diagnostic image the patient must be positioned in the scanning range. With therapy devices, the effective range can be a range within a radiation bundle for instance. A therapeutic radiation, for example, with x-rays or electron beams, can be undertaken in the effective range.

Positioning facilities generally include a table top, upon which the patient can lie or if necessary sit, in order to be positioned in the effective range of the medical device. The 'effective range' is a patient or body, of which a CT recording is to be generated, that is located in the effective range. The table top can be mounted to be height-adjustable, rotatable and tiltable. The table top may be moved in the longitudinal (transverse) direction. Table tops may be improved in the transverse direction.

Motor drives are usually used to change the position of the table top. The motor drives spare an operator from expending effort on a manual positioning, particularly with patients lying thereupon. The motor drives adjust the position. The motor drives are controlled by a control facility. The control facility can be operated by a wide variety of input devices, for example, joystick, mouse, keyboard, or touch screen. The controllers do not provide direct patient contact during control. A manual displacement and a motorized displacement of the table top have been used to provide direct patient contact. Due to the coupled motor drive, an operator must overcome the sluggishness of the motor drive, for example, motor or transmission.

DE 199 29 654 discloses coupling the motor drive to the table top by electromagnetic or mechanical clutches. If the table is to be moved manually, it is decoupled from the drive by a clutch. Only the frictional forces of the table mount, for example, rollers, linear guides or ball-bearings and of the drive train, for example, toothed belts or toothed racks, must be overcome. The clutch must first be released by manual activation or effort. The clutch involves more constructional outlay.

SUMMARY

The present embodiments may obviate one or more of the drawbacks or limitations in the related art. For example, in one embodiment, a patient positioning facility enables both a motorized and also a manual displacement of the table top. Both the motorized and manual displacement of the table top can be simultaneously operated with minimal effort and with minimal constructional outlay.

The coupling between the motor drive and table top of a patient positioning facility includes elastically deformable or flexible components. When a force is exerted on the table top, by pushing it manually for instance, a minimal displacement of the table top can hereby be effected, the extent of which depends on the degree of flexibility and/or elasticity of the coupling. For example, positioning facilities may have a table top that is displaced by a motor-driven plastic belt or a plastic band. The elasticity of these plastic components in the drive train allows flexibility in the direction of movement by enabling the table top to be moved slightly even if the motor drive is stationary.

In one embodiment, a patient positioning facility uses movements of the table top to initiate control of the drive. The movements are carried out between the drive and the table top within the scope of flexibility or elasticity of the coupling. Control is initiated by manually produced movements of the table top, which were not generated by the motor drive. The manually produced movements occur despite the stationary motor drive. Only the actual position of the table top needs to be compared with the current setting of the motor drive. "Setting the motor drive" is a variable, upon which the positioning of the table top is dependent, for example, an angle of rotation of the drive shaft.

A measurement system, for example, a cable absolute value generator, rotary potentiometer, linear potentiometer, or optical absolute value generator may be provided to record the table position in the case of motorized positioning facilities. A further measurement system, for example, a resolver, may be provided to record the setting of the motor drive.

These two measurement systems provide exactly the position information that is required.

Position changes produced by the motor drive are a fixed assignment between the signal of the measurement system for the table position and the signal of the measurement system for the motor drive setting. The mutual assignment of the two signals can be logged by a calibration measurement for instance. The two signals can be logged during the operation of the positioning facility.

A manual displacement of the table top produces a signal on the measurement system for the table position. The signal does not correspond to the current signal of the measurement system for the motor drive setting according to a calibrated context. With such a deviation of the signals of the two measurement systems, the direction of the manual displacement can be determined on the basis of the algebraic sign of the deviation. The manually applied shifting force can be determined on the basis of the degree of the deviation. The direction and displacement force are then used to control the motor drive such that a manual displacement of the table top is supported by a motor force. Servo support is thus achieved in this way.

The motorized servo support allows a minimal displacement force to be realized even in the case of a sluggish drive and displacement mechanism. The actual displacement force can even be controlled by the controller of the motor drive such that it lies below the displacement force that would, for example, be produced in the case of the motor drive decoupled by a clutch.

Already available measurement systems may be used so that there is no need for additional separate measurement systems to be provided. The present embodiments can be implemented exclusively using the motor drive controller. Depending on the design, the present embodiments can be implemented by a simple reprogramming of the motor controller software.

A clutch is no longer necessary for decoupling the table top and motor drive, so that constructional outlay, material costs, installation outlay and maintenance costs are reduced.

DETAILED DESCRIPTION

Figure 1:
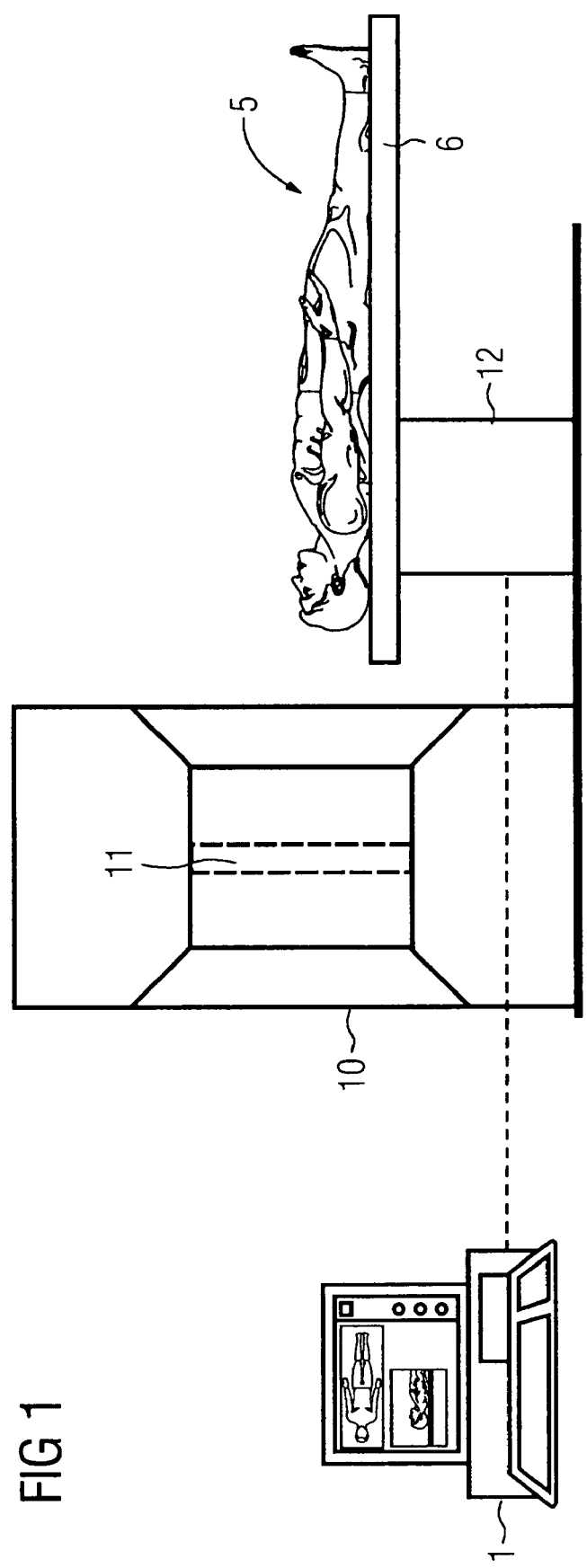
FIG. 1 is a schematic diagram of a medical device having a positioning facility.

FIG. 1 is a diagram representation of a medical device, namely a computer tomography device ("CT Device") 10, together with the patient positioning facility. In one embodiment, as shown in FIG. 1, the CT device 10 includes an examination port 11. An effective range of the device is disposed in the examination port 11. The effective range is the area in which a patient or body needs to be positioned in order to be able to generate a CT recording.

A patient positioning facility is provided with the computer tomography device 10. The patient positioning facility includes a table top 6 that is mounted in a moveable manner on a bed base 12. A patient 5 to be examined lies on the table top 6. By moving the table top 6, the patient can be moved into the examination port 11, in order to generate a CT recording.

The table top 6 is moved by way of a motor drive. The motor drive is controlled by a control facility 1. An operator can operate the control facility 1, which can be a computer for instance, as shown in FIG. 1, by different input devices.

Figure 2:
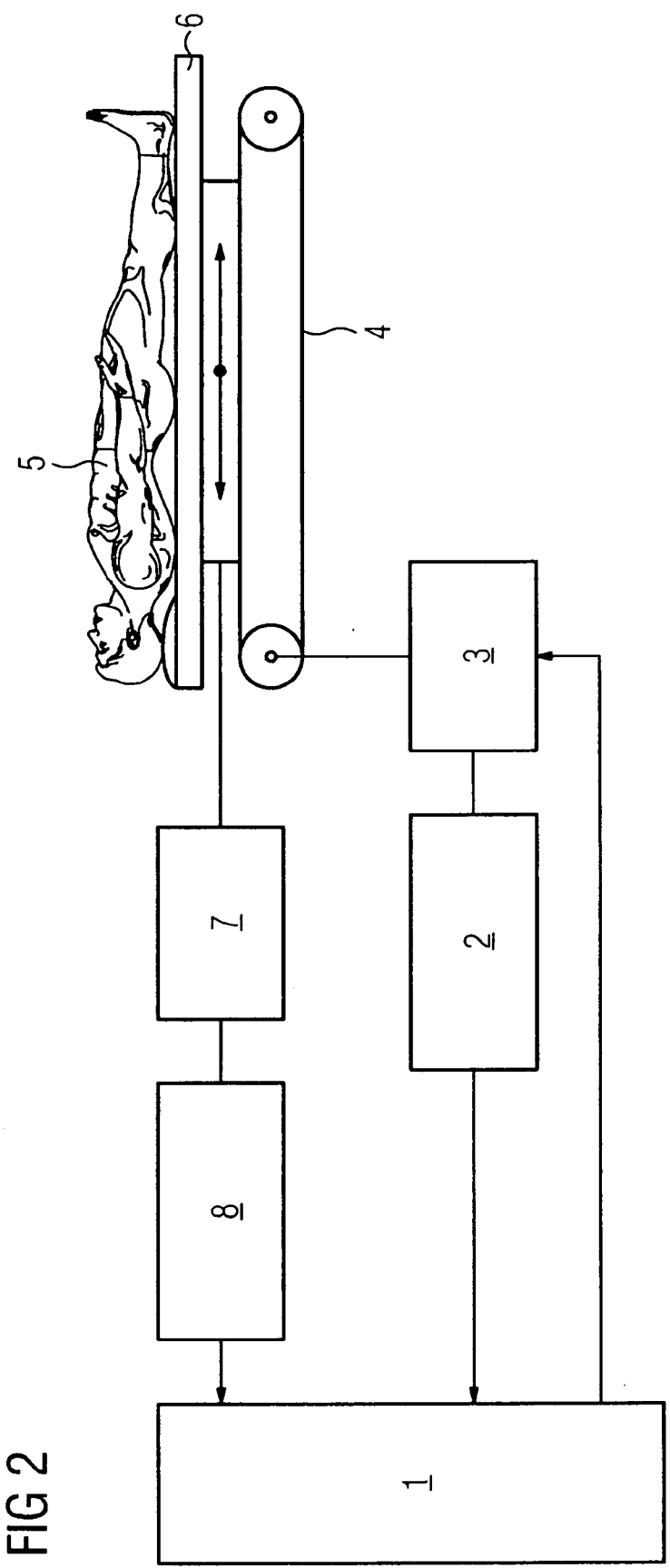
FIG. 2 is a schematic diagram of the motorized support of the positioning facility.

FIG. 2 is a schematic diagram of the controller of the motor drive of the table top 6. The table top 6, upon which the patient lies 5, can be moved by a bed drive 4. The bed drive 4 is a belt or a band which runs around two guide rollers. The direction of displacement is indicated by a horizontal double-ended arrow.

The bed drive 4 is driven by an electric motor 3. The electric motor 3 is coupled to one of the two guide rollers. The electric motor 3 is designed as a servomotor. The respective current setting of the electric motor 3, as an angle of rotation, is recorded by a resolver 2. Resolvers may be used as measurement systems for the setting of servomotors. The resolver 2 supplies the respective current setting of the electric motor 3 as an output signal to the control facility 1. The control facility 1 knows the respective current setting of the electric motor 3.

The position of the table top 6 is recorded by a further measurement system, which is a position sensor 7. The position sensor 7 is connected to a position sensor 8, which releases the information relating to the position of the patient bed 6 as an output signal to the control facility 1. The respective current position of the patient bed 6 is known in the control facility 1.

A characteristic curve is stored in the control facility 1 in a calibrator. The characteristic curve of the association between the setting of the electric motor 3 and the position of the patient bed 6 can be determined by the calibrator when there is no external force effect on the table top 6. The characteristic curve can be stored as tabular data or mathematical formulae for instance. During commissioning, maintenance or assembly of the positioning facility, it can be determined within the scope of a calibration measurement.

The control facility 1 can determine on the basis of the characteristic curve whether an external displacement force is acting upon the table top 6, since the position signal no longer corresponds to the signal for the setting of the electric motor 3 in accordance with the characteristic curve. The position of the patient bed 6 no longer corresponds to the assigned setting of the electric motor 3 according to the characteristic curve.

In one embodiment, the signal for the position of the table top 6 is compared, as described, with that of the setting of the electric motor 3. The comparison is drawn between absolute values.

In one embodiment, the control facility 1 determines a change in the position of the table top 6 as well as a change in the setting of the electric motor 3. The control facility 1 then compares, on the basis of the characteristic curve, whether the change in position of the table top 6 corresponds to that of the setting of the electric motor 3 in accordance with the characteristic curve.

In one embodiment, the control facility 1 determines whether a change in the position of the table top 6 is taking place. If the position of the table top 6 is taking place, the control facility 1 subsequently determines whether a change in the setting of the electric motor 3 is carried out. If the setting of the electric motor 3 is not being carried out, it can already be controlled without further accessing the calibrator of the electric motor 3. An at least initial servo-support with a particularly short reaction time can be realized without an evaluation of the characteristic curves being carried out first.

Further embodiment variants of the control facility 1 can be readily deduced for the person skilled in the art and result from knowledge of control engineering.

Various embodiments described herein can be used alone or in combination with one another. The forgoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:

1. A device for motorized support of a patient positioning facility, the device comprising:
    a control facility,
    an electric motor drive that is operable to be controlled by a control signal of the control facility,
    a measurement device that is operable to record a setting of the electric motor drive and to generate an output signal representing the setting of the motor drive while the motor drive is stationary,
    a moveable patient bed,
    a bed drive that is operable to be driven by the electric motor drive and that is operable to displace the patient bed, and
    a position sensor that is operable to record the position of the patient bed and to generate an output signal representing the position of the bed,
    wherein position changes produced by the electric motor drive are characterized by a fixed assignment between the output signal of the position sensor representing the position of the bed and the output signal of the measurement device representing the setting of the motor drive,
    wherein the bed drive is flexible and/or elastic with respect to the displacement direction of the patient bed such that the output signal of the measurement device and the output signal of the position sensor are operable to be fed to the control facility, and
    wherein the control facility is operable to generate the control signal for the electric motor drive as a function of a change in the output signals with respect to one another such that a manual movement of the patient bed allowed by the flexible and/or elastic nature of the bed drive is detected by the position sensor while the motor drive is stationary, the control facility operable to initiate operation of the electric motor drive in response to the manual movement of the patient bed while the motor drive is stationary.

2. The device as claimed in claim 1, wherein the control facility is operable to record a change in the output signal of the position sensor such that it records a change in the output signal of the measurement device and operable to generate the control signal for the electric motor drive as a function of the respective change in the output signals.

3. The device as claimed in claim 1, wherein the control facility is connected to a calibrator which is operable to generate the control signal for the electric motor drive as a function of the output signals of the position sensor and the measurement device.

4. The device as claimed in claim 3 wherein the control facility is operable to generate the control signal for the electric motor drive as a function of a change in the output signal of the position sensor, which does not correspond to a simultaneous change in the output signal of the measurement device.

5. The device as claimed in claim 1, wherein the electric motor drive is servomotor.

6. The device as claimed in claim 1 wherein the measurement device includes a resolver.

7. The device as claimed in claim 1 wherein the bed drive includes a belt or band.

8. The device as claimed in claim 1 wherein the bed drive is at least partially composed of plastic.

9. A method for motorized support of a patient positioning facility, comprising:
   recording a position of a patient bed moved by a manual movement and generating an output signal representing the position of the patient bed;
   recording a setting of an electric motor drive which is operable to move the patient bed and generating an output signal representing the setting of the electric motor drive while the motor drive is stationary;
   generating a control signal for the electric motor drive as a function of the output signal for the position of the patient bed and the output signal for the setting of the electric motor drive to initiate operation of the electric motor drive in response to the manual movement of the patient bed while the motor drive is stationary, and
   positioning the patient bed according to the generated control signal,
   wherein position changes produced by the electric motor drive are characterized by a fixed assignment between the output signal of a position sensor for the bed position and the output signal of a measurement device for the motor drive setting.

10. The method as claimed in claim 9, comprising: recording a change in the position of the patient bed.

11. The method as claimed in claim 10, wherein the control signal is a function of the change in the position of the patient bed.

12. The method as claimed in claim 9 comprising: accessing a calibrator with the control signal being generated on the basis of access to the calibrator.

13. The method as claimed in claim 9 with the control signal being generated as a function of a change in the position of the patient bed, which does not correspond to a simultaneous change in the setting of the electric motor drive.

14. The device as claimed in claim 6, wherein the resolver is operable to record an angle of rotation of the electric motor drive.

15. The method as claimed in claim 11, comprising: accessing a calibrator, with the control signal being generated on the basis of access to the calibrator.

16. The method as claimed in claim 12, with the control signal being generated as a function of a change in the position of the patient bed, which does not correspond to a simultaneous change in the setting of the electric motor drive.

17. A device for motorized support of a patient positioning facility:
   a first measurement device that is operable to produce a first output signal based on a position of a patient bed;
   a second measurement device that is operable to produce a second output signal based on a setting of an electric motor drive, while the motor drive is stationary, that is operable to move the patient bed; and
   a control facility is operatively coupled to the first and second measurement device, and
   wherein position changes produced by the electric motor drive are characterized by a fixed assignment between the first output signal and the second output signal,
   wherein the control facility is operable to generate a control signal for the electric motor drive as a function of a change in the first and second output signals with respect to one another such that a manual movement of the patient bed allowed by the flexible and/or elastic nature of the bed drive is detected by a position sensor while the motor drive is stationary, the control facility operable to initiate operation of the electric motor drive in response to the manual movement of the patient bed while the motor drive is stationary.

18. A device for motorized support of a patient positioning facility according to claim 17, wherein the second measurement device includes a resolver.

19. A device for motorized support of a patient positioning facility according to claim 17, wherein the first measurement device includes a cable absolute value generator, rotary potentiometer, linear potentiometer, or optical absolute value generator.

20. The device as claimed in claim 1, wherein the control facility is operable to determine a direction of the manual movement on the basis of a deviation of the output signals of the position sensor and the measurement device.

21. The device as claimed in claim 1, wherein the measurement device is operable to record an angle of rotation of the electric motor drive.

* * * * *